United States Patent
Renimel et al.

(10) Patent No.: US 6,413,519 B1
(45) Date of Patent: Jul. 2, 2002

(54) **USE OF AN EXTRACT OF THE PLANT *TERMINALIA CATAPPA* IN THE COSMETIC AND PHARMACEUTICAL FIELDS, ESPECIALLY THE DERMATOLOGICAL FIELD**

(75) Inventors: Isabelle Renimel, Trainou; Marc Olivier, Les Angles; Patrice Andre, Neuville Aux Bois, all of (FR)

(73) Assignee: Parfums Christian Dior, Paris (FR)

( * ) Notice: Subject to any disclaimer, the term of this patent is extended or adjusted under 35 U.S.C. 154(b) by 0 days.

(21) Appl. No.: 09/102,617

(22) Filed: Jun. 23, 1998

Related U.S. Application Data

(63) Continuation-in-part of application No. PCT/FR97/02342, filed on Dec. 18, 1997.

(30) Foreign Application Priority Data

Dec. 20, 1996  (FR) ............................................. 96 15793

(51) Int. Cl.$^7$ ........................ A61K 35/18; A61K 39/385
(52) U.S. Cl. .................................................. 424/195.1
(58) Field of Search ...................... 424/195.1

(56) References Cited

U.S. PATENT DOCUMENTS

| | | | | |
|---|---|---|---|---|
| 5,073,545 A | * | 12/1991 | Arima et al. .................. | 514/27 |
| 5,166,139 A | * | 11/1992 | Bombardelli et al. ......... | 514/26 |
| 5,286,629 A | * | 2/1994 | Denis et al. .................. | 435/7.1 |
| 5,693,327 A | * | 12/1997 | Shah ........................ | 424/195.1 |
| 5,705,170 A | * | 1/1998 | Kong et al. .................. | 424/401 |
| 6,217,876 B1 | | 4/2001 | Pauly ..................... | 424/195.1 |
| 2001/0002265 A1 | | 5/2001 | Pauly | |

OTHER PUBLICATIONS

Medline Abstract AN: 96285609, Liu, T. Y. et al., Jul. 1996.*
HCAPLUS Abstract AN: 1996:191003, Shimomura, K., Abstract of JP8012586 A2, Jan. 1996.*
HCAPLUS Abstract AN: 1996: 303954, Nanba, T. et al., Abstract of JP 8067617 A2, Mar. 1996.*
S.K. Puri et al, Mechanisms of Aging and Dev. 15(1981), pp. 239–242.
J.S. Baumstark et al, Biochim.Biophys. Acta 77(1963), pp. 676–679.
B. Bieth et al, Biochem Med. 11(1974) pp 350–377.
C. Franck et al, Biol.Chem.Hoppe–Seyler, vol. 369 (1988), pp. 667–682.
J.F. Uthe et al, Can. J. Biochem. (1971), pp. 776–784.
E.A. Dennis, J. Lipids.Res. (1973), pp. 152–159.
C.W. Taylor et al, Brit. Med. Bull. (1983), pp. 219–222.
Hitchcock, "Reduction in Basal Adenylate Cyclase Activity During the Immunologic Release of Histamine from Guinea Pig Lung[1,2]".
The Journal of Immunology, 1977, pp. 578–583.
Prazeres, Emir, 122CA:248344, Jan. 1995.*

* cited by examiner

*Primary Examiner*—Russell Travers
(74) *Attorney, Agent, or Firm*—Dennison, Scheiner & Schultz

(57) ABSTRACT

A cosmetic composition containing an extract of the plant *Terminalia catappa* is found to be useful for combating skin ageing and the phenomena of irritation, inflammation, allergic reaction and hyperpigmentation. It also has been found to have a slimming effect and is useful in the treatment of freckles.

10 Claims, No Drawings

USE OF AN EXTRACT OF THE PLANT *TERMINALIA CATAPPA* IN THE COSMETIC AND PHARMACEUTICAL FIELDS, ESPECIALLY THE DERMATOLOGICAL FIELD

This application is a Continuation-in-Part application of the International PCT application PCT/FR97/02342 filed on Dec. 18, 1997, which in turn claims the French priority of French patent application No. 96.15793 of Dec. 20, 1996.

BACKGROUND OF THE INVENTION

The invention relates to uses of an extract of the plant *Terminalia catappa* in the cosmetic and pharmaceutical fields, especially the dermatological field.

It relates more precisely to uses of an extract of this plant as a cosmetic agent.

The plant *Terminalia catappa* belongs to the Combretaceae family, which is found particularly in New Caledonia.

The systematic experiments carried out by the inventors have made it possible to demonstrate a number of surprising enzymatic actions of the extracts of this plant, particularly inhibitory actions on several enzymes, especially phospholipase $A_2$, 5'-lipoxygenase, tyrosinase and 3',5'-cAMP phosphodiesterase, which has made it possible to consider its use in cosmetic and pharmaceutical products, especially dermatological products.

Phospholipase $A_2$ ($PLA_2$) is an enzyme produced by membrane cells. It predominates in cells associated with inflammation phenomena, such as mastocytes. Through its action it releases the arachidonic acid bound to the membrane phospholipids. This acid then metabolizes to different lipidic mediators of inflammation and allergy, such as leukotrienes and prostaglandins.

Like $PLA_2$, 5'-lipoxygenase, hereafter called "lipoxygenase", is a membrane enzyme. It is involved in the "inflammation cascade" downstream of the release of arachidonic acid by $PLA_2$, converting this acid to leukotrienes, which are mediators of inflammation.

3',5'-cAMP phosphodiesterase, hereafter called "phosphodiesterase" or "PDE", is the enzyme which converts cAMP—a second messenger involved in controlling the cell metabolism—to inactive AMP. Consequently, the inhibition of PDE by an inhibitor makes it possible to maintain a high intracellular level of cAMP, which has the effect especially of activating the protein kinases A and, via this process, makes it possible to promote lipid degradation.

Furthermore, it is also known that cAMP plays a part in counteracting certain inflammatory processes (M. Hitchcock, J. Immunol. (1977) 188 557). Also, it has been described that phosphodiesterase increases with age (S. K. Puri and L. Volicer, Mechanisms of Aging and Dev. (1981) 15 239). The inhibition of phosphodiesterase will therefore make a contribution to combating the effects of ageing, particularly on the skin.

Tyrosinase is the key enzyme in the synthesis of melanin and hence in the metabolism of skin pigmentation. In cosmetics, the inhibition of tyrosinase by appropriate agents has applications in the local treatment of skin hyperpigmentations such as liver spots.

SUMMARY OF THE INVENTION

Thus it has been demonstrated by the inventors that, by virtue of their inhibitory action on the above-mentioned enzymes, extracts of the plant Terminalia catappa are of great value in cosmetics and therapeutics.

In fact, through the discovery of the inhibitory activity of extracts of the plant Terminalia catappa on the action of enzymes, the invention provides different solutions in the cosmetic and therapeutic fields, especially the dermatological field. As regards the inhibition of phospholipase $A_2$ on the one hand and lipoxygenase on the other, the compositions according to the invention thus have a dual action in the process of formation of the mediators of skin allergy and inflammation, by limiting or blocking this process.

The inhibition of phosphodiesterase (PDE) gives the compositions of the invention a slimming, anti-inflammatory and anti-ageing action. The inhibition of tyrosinase gives them a skin depigmenting effect.

Other advantages of the invention will become apparent from the iption and the Examples which follow.

DETAILED DESCRIPTION OF THE INVENTION

Thus, according to one of its essential characteristics, the invention relates to cosmetic compositions containing an extract of the plant Terminalia catappa in the presence of a cosmetically acceptable vehicle.

It is essentially the leaves which are found to be of value in the preparation of the extracts of the invention.

The extract is advantageously obtained by maceration of the plant or part of the plant in a solvent or solvent mixture, followed by filtration. The solvent of the solution obtained can be evaporated off, if necessary, to give the dry extract.

The evaporation will preferably be performed under reduced pressure.

The following may be mentioned as solvents which are advantageously used:

water chlorinated solvents, especially dichloromethane ethers such as ethyl or diisopropyl ether acetone $C_2$ to $C_8$ esters such as ethyl acetate and butyl acetate $C_1$ to $C_6$ alcohols such as methanol, ethanol and isopropanol $C_2$ to $C_6$ polyols such as propylene glycol or glycerol.

The plant extract can also be obtained by the so-called supercritical carbon dioxide extraction technique.

In one advantageous embodiment, this composition comprises from 0.001 to 10% by weight and particularly from 0.02 to 1% by weight of dry plant extract, based on the total weight of the final composition.

Furthermore, the experiments carried out by the inventors have clearly shown that not only the extraction yield but also the enzymatic activity of the extract is related to the nature of the solvent used. The attached Examples clearly show the effect of the choice of solvent on the enzymatic activity of the extract.

The compositions according to the invention can be formulated in any form acceptable for their use in cosmetology. In particular, the composition can be in a form appropriate for topical application, specifically in the form of a cream or gel and particularly a cream or gel for the face, hands, bust or body.

According to another aspect, the invention relates to the use of the plant extract as a cosmetic agent, said agent being incorporated in a cosmetic composition as defined above.

This cosmetic agent will be used especially in all applications which are aimed in particular at inhibiting the action of phospholipase $A_2$ and/or lipoxygenase and/or phosphodiesterase and/or tyrosinase.

The compositions according to the invention will also be used to combat the effects of skin ageing, especially by preserving or improving the biomechanical properties of the skin, particularly its elasticity, by delaying the appearance of wrinkles or reducing their depth and by improving the firmness of the skin.

They will also be used for the care of sensitive skin, especially by reducing or eliminating the phenomena of irritation, inflammation or allergy which generally manifest themselves on the skin in the form of red blotches or burning or smarting sensations.

They may also be used to achieve slimming on different parts of the body, particularly the hips. They may also be used for the purpose of reducing or eliminating freckles.

Thus the cosmetic compositions of the invention will be used especially for any cosmetic applications which are aimed at inhibiting the activity of the above-mentioned enzymes.

Thus, according to another aspect, the invention relates to cosmetic compositions intended for skin care and particularly for combating the effects of skin ageing or inflammation phenomena.

They are also found to be of value for their slimming action or their depigmenting action.

As seen previously, it has been possible to correlate the efficacy of the above-described cosmetic compositions with a number of enzymatic activities. The demonstration of these enzymatic activities has also made it possible to consider using the above-defined extracts for the preparation of pharmaceutical compositions, especially dermatological compositions, in which such activities are desired. The experiments carried out by the inventors of the present invention have confirmed the efficacy of these pharmaceutical compositions.

Thus it has been possible to correlate the inhibition of phospholipase $A_2$ and the inhibition of 5'-lipoxygenase with efficacy in the prevention and treatment of inflammation phenomena.

It has been possible to correlate the inhibition of tyrosinase with an action in the local treatment of skin hyperpigmentation.

The inhibition of PDE results in the maintenance of a high intracellular level of cAMP. This leads to a variety of effects concerning the skin, particularly slimming, anti-ageing and anti-inflammatory effects.

Thus, according to another essential characteristic, the invention further relates to the use of an extract of the plant *Terminalia catappa* for the preparation of a pharmaceutical composition, especially dermatological composition, intended for the treatment of the effects of intrinsic or actinic skin ageing, for the prevention or treatment of the skin manifestations of allergies and inflammations, for the reduction of excess fat or for the treatment of freckles in order to reduce or eliminate them, said extract being incorporated in a pharmaceutically acceptable vehicle.

For these different applications the pharmaceutical composition advantageously has an inhibitory activity on phospholipase $A_2$ and/or lipoxygenase and/or phosphodiesterase and/or tyrosinase.

In one variant the invention relates to the use of an extract of Terminalia catappa for the preparation of a pharmaceutical composition, especially dermatological composition, intended for the treatment and prevention of allergic manifestations, particularly skin allergy.

This type of application is directly associated with inhibition of the lipidic mediators of inflammation.

In all the applications in the pharmaceutical field, especially the dermatological field, the compositions used are preferably compositions for topical application which are intended for application to the skin. Furthermore, the plant extracts used for their preparation are obtained in the same manner as the extracts used in the cosmetic field, from the same parts of the plant, and are introduced into a pharmaceutically acceptable vehicle, especially dermatologically acceptable vehicle, at concentrations of between 0.001% and 10% by weight and particularly of between 0.02% and 1% by weight of dry extract of said plant or part of the plant.

As in the case of the cosmetic applications, the extraction solvent will be chosen according to the type of enzymatic activity which is to be emphasized in the action of the pharmaceutical composition.

According to another variant, the invention relates to a method of treating cellulite, which comprises the application on the part of the body to be treated of a composition comprising an effective amount of an extract of the plant *Terminalia catappa*.

In said method, the concentration of the extract and the nature of the solvent used to obtain said extract are advantageously chosen so that the composition has an inhibitory action on at least one of the enzymes selected from the group consisting of phospholipase $A_2$, lipoxygenase and phosphodiesterase.

As for the other applications, the extract is advantageously an extract of leaf and the composition contains advantageously from 0.001% to 10% by weight, and preferably from 0.02% to 1% by weight, of a dry extract of said plant.

The Examples which follow are given purely in order to illustrate the invention.

Unless indicated otherwise, the proportions given in the Examples of compositions are expressed as percentages by weight.

EXAMPLE 1

Preparation of an extract according to the invention 1 g of leaves of the plant Terminalia catappa, dried and ground beforehand, is introduced into 200 ml of solvent. The suspension is left to stand at room temperature for 4 hours, with moderate stirring. The mixture is subsequently filtered and the solvent is then evaporated off from the resulting filtrate under reduced pressure. The dry extract is then recovered. The compositions according to the invention can be prepared using either the optionally concentrated solution of plant extract in the extraction solvent, or the dry extract.

Extracts were prepared using 2 different solvents: water and methanol.

EXAMPLE 2

Demonstration of the inhibitory activity of the extracts on different enzymes 2.1. Extracts used As the enzymatic inhibition tests are performed in aqueous media, it is necessary to use water-miscible extraction solvents.

Thus, by following the procedure described in Example 1, three different extracts were prepared with water, methanol and DMSO respectively. The concentration of these extracts is then adjusted to 0.5% of dry plant extract, either by addition or by evaporation of the extraction solvent.

All the tests described below were carried out in triplicate. The values reported are arithmetic means.

2.2. Inhibition of elastase a) Principle of the test:

The techniques for demonstrating the inhibition of elastase have been described by various authors (BAUMSTARK, J. S. et al., Biochim. Biophys. Acta (1963), 77, 676; BIETH, B. et al., Biochem. Med., (1974), 11, 350; C. FRANCK, I. BYRJALSEN, Biol. Chem. Hoppe Seyler, (1988) 369 (8) 677–82).

The active principle is as follows: a substrate is brought into contact with elastase in an aqueous medium and then, after incubation, the reaction products are measured.

In the present case the substrate is N-succinyl-(Ala)$_3$-paranitroanilide, available from Sigma (ref.: S 4760), in a solution containing 0.5 mg/ml in 0.2 M Tris-HCl buffer of pH 8.8. The elastase added to the reaction medium releases the paranitroaniline and the peptide residue. The course of the reaction is observed on a Uvikon 941® spectrophotometer (Kontron S.A.) at a wavelength λ of 379 nm.

The composition of the reaction medium is as follows:
substrate solution (0.5 mg/ml of buffer): 200 µl
Tris-HCl buffer: 600 µl
extraction solvent: 100 µl The extraction solvent may or may not contain the effector, i.e. the extract of the plant *Terminalia catappa* at a concentration of 0.5% by weight, depending on whether the test with effector or the test without effector (baseline activity of the enzyme) is being carried out.

100 µl of the enzyme solution, containing 35 U/ml in the Tris-HCl buffer, are added to these 900 µl of reaction medium immediately before use.

The kinetics of release of paranitroaniline are then measured by the absorption of monochromatic light of wavelength 379 nm on a spectrophotometer, enabling the percentage inhibition $I_E$ to be calculated according to the following formula:

$$I_E = \frac{\Delta AbB/\min - \Delta AbE/\min}{\Delta AbB/\min} \times 100$$

in which ΔAbB/min is the difference in absorbance per minute of the reaction medium for the baseline activity and ΔAbE/min is the difference in absorbance of the reaction medium for the test with effector. The absorbance values considered are those corresponding to the linear period of the change in absorbance as a function of time.

The results are shown in Table I below.

2.3. Inhibition of phospholipase $A_2$

In accordance with the principle of the test (UTHE, J. F. and MAGEE, W. L., Can. J. Biochem. (1971),49, 776; DENNIS, E. A., J. Lipids Res., (1973), 14 152), the enzyme is brought into contact with a phospholipid. The latter is then converted to lysolecithin with the release of a fatty acid insoluble in the reaction medium. This reaction can therefore be followed by turbidimetry on a spectrophotometer, for example at a wavelength of 360 nm.

The composition of the reaction medium is indicated below. All the solutions are prepared in distilled water:
14 mM solution of L-(dimyristoyl)phosphatidylcholine (substrate): 600 µl
0.67 M sodium chloride solution: 150 µl
66 mM calcium chloride solution: 200 µl
distilled water: 850 µl
solvent, without or with effector at 0.5%: 100 µl
100 µl of the enzyme solution, at a concentration of 96 U/ml in distilled water, are added to this medium immediately before use.

As in the case of the inhibition of elastase, the reaction kinetics are followed on a Uvikon 941® spectrophotometer at a wavelength of 360 nm.

The percentage inhibition $I_p$ of phospholipase $A_2$ is determined by calculation according to a formula analogous to that for the inhibition of elastase:

$$I_p = \frac{\Delta AbB/\min - \Delta AbE/\min}{\Delta AbB/\min} \times 100$$

in which ΔAbB and ΔAbE are as defined above.

The results are shown in Table I below.

2.4. Inhibition of 5'-lipoxygenase

As explained earlier, lipoxygenase is involved in the formation of mediators of inflammation, particularly leukotrienes, from arachidonic acid.

In the test for demonstrating the inhibition of this enzyme (C. W. Taylor, H. R. Morris, Brit. Med. Bull. (1989) 39 219–222; J. Magee, Methods of Enzymatic Analysis, H. U. Bergmayer Ed., (1965) pp. 411–4, Academic Press, N.Y.), the substrate used is linoleic acid, which is converted to 5-hydroperoxy-6,8,11,14-eicosatetraenoic acid (5-HPETE) in the presence of the enzyme.

Composition of the reaction medium:
linoleic acid (substrate), 0.5 mM solution: 2000 µl
0.2 M borate buffer of pH 9: 950 µl
solvent, without or with effector at 0.5% in the borate buffer: 100 µl The above linoleic acid solution is prepared by first partially salifying the linoleic acid in methanol in the presence of sodium hydroxide, and then introducing it into the borate buffer.

100 µl of the solution of the enzyme 5'-lipoxygenase, at a concentration of 10 U/ml in the borate buffer, are then added immediately before use.

As in the previous tests, the absorbance of the media is measured as a function of time and the percentage inhibition IL of 5'-lipoxygenase is calculated for the linear part of the change in absorbance.

The results are shown in Table I below.

2.5. Inhibition of Phosphodiesterase (PDE)

The principle of this test is based on the hydrolysis of cyclic 3',5'-adenosine monophosphate (cAMP) to adenosine monophosphate (AMP). The formation of AMP is measured by HPLC analysis.

The composition of the reaction medium is indicated below. The solutions of the reagents are prepared in 0.05 M Tris-HCl buffer of pH 7.5.
solution of cAMP (substrate) at 0.25% in the buffer 80 µl
solvent, without or with effector at 0.5% 80 µl
Tris-HCl buffer 480 µl
160 µl of PDE, at a concentration of 0.5 U/ml in the Tris-HCl buffer, are added to this medium immediately before use.

At time t=5 minutes, the quantity of AMP formed is measured by calculating the surface area of integration of the AMP peak on the chromatogram produced by the HPLC apparatus (KONTRON S.A.).

The level of inhibition $I_A$ of PDE by the effector can then be estimated according to the following formula:

$$I_A = \frac{SAMP_b - SAMP_e}{SAMP_b} \times 100$$

in which $SAMP_b$ represents the surface area of integration of the AMP peak for the baseline activity of the enzyme (without effector) and $SAMP_e$ represents the surface area of integration of the AMP peak for the activity of the enzyme in the presence of the effector.

The results obtained are shown in Table I below.

2.6. Inhibition of Tyrosinase

The principle of this test is based on the formation of dopachrome from L-tyrosine by the action of tyrosinase.

It is pointed out that, in the presence of tyrosinase and oxygen, L-tyrosine oxidizes to L-DOPA, which in turn oxidizes to dopaquinone, again through the action of tyrosinase. Dopaquinone then cyclizes to cyclodopa, which oxidizes to dopachrome; this is a precursor of melanins and absorbs light at a wavelength of 480 nm.

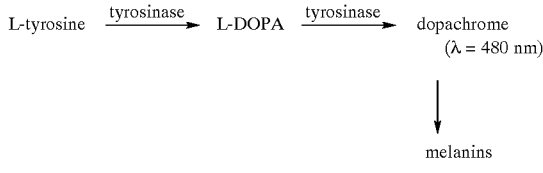

The formation of dopachrome can therefore be followed by spectrophotometry.

For this method, reference may be made in particular to the publications by S. H. Pomerantz, Arch. Biochem. Biophys. (1974) 160 73–82, or J. Barber, J. Invest. Dernatol. (1984) 83 145–149.

The composition of the reaction medium is indicated below. The solutions of the reagents are prepared in 0.02 M phosphate buffer of pH 6.9.

solution of L-tyrosine (1st substrate) at 1 mM in the buffer 333 µl solution of L-DOPA (2nd substrate) at 1 mM in the buffer 333 µl solvent, without or with effector at 0.5% 333 µl 33 µl of tyrosinase solution, at a concentration of 2400 U/ml in the phosphate buffer, are added to this reaction medium immediately before use.

The kinetics of formation of dopachrome are then measured by the absorption of monochromatic light of wavelength 480 nm on a Uvikon 941 spectrophotometer (KONTRON S.A.), making it possible to calculate, for the linear part of the change in absorbance as a function of time, the percentage inhibition $I_T$ of tyrosinase according to the following formula:

$$I_T = \frac{\Delta AbB/\min - \Delta AbE/\min}{\Delta AbB/\min} \times 100$$

in which ΔAbB/min is the difference in absorbance per minute of the reaction medium for the baseline activity of the enzyme (without effector) and ΔAbE/min is the difference in absorbance of the reaction medium for the test with effector.

The results are shown in Table I below.

TABLE I

Level of enzymatic inhibition by the extracts of the invention

| | Extract | | |
|---|---|---|---|
| | $E_{water}$ | $E_{methanol}$ | $E_{DMSO}$ |
| $I_E$ (elastase) | 8 | 1 | 15 |
| $I_P$ (PLA$_2$) | 85 | 36 | 68 |
| $I_L$ (lipoxygenase) | — | 19 | 73 |

TABLE I-continued

Level of enzymatic inhibition by the extracts of the invention

| | Extract | | |
|---|---|---|---|
| | $E_{water}$ | $E_{methanol}$ | $E_{DMSO}$ |
| $I_T$ (tyrosinase) | 40 | — | — |
| $I_A$ (PDE) | 89 | 90 | 66 |

$E_{water}$: 0.5% aqueous extract
$E_{methanol}$: 0.5% methanol extract
$E_{DMSO}$: 0.5% DMSO extract The results shown in Table I above demonstrate the value of the extracts according to the invention in the cosmetic and pharmaceutical fields, especially the dermatological field, wherever the action of certain enzymes is to be blocked, reduced in magnitude or regulated.

More precisely, it is clearly apparent that each of the five enzymes tested, with the exception of elastase, is substantially inhibited by at least one of the extracts tested.

The action of the extracts of *Terminalia catappa* is particularly significant on the inhibition of phosphodiesterase and phospholipase A$_2$, but the aqueous extract is also active on the inhibition of tyrosinase and the DMSO extract is very active on the inhibition of lipoxygenase.

Therefore the extracts of *Terminalia catappa* can advantageously be used for the different applications mentioned above which follow from the inhibition of the enzymes in question.

EXAMPLE 3

| Cosmetic anti-wrinkle gel | |
|---|---|
| Dry extract of Example 1, methanol fraction | 0.05 g |
| Carbomer | 0.3 g |
| Glycerol | 3.0 g |
| Tetrasodium EDTA | 0.05 g |
| Aqueous extract of witch hazel | 3.00 g |
| Polymethyl methacrylate | 1.00 g |
| Perfumes, preservatives, color, neutralizer | qs |
| Distilled water | qsp 100 g |

This gel has a soothing anti-wrinkle effect.

EXAMPLE 4

| Anti-wrinkle cream for the face | |
|---|---|
| Dry extract according to Example 1, aqueous fraction | 0.5 g |
| Glyceryl stearate + PEG 100 stearate | 5.0 g |
| Cetyl alcohol | 1.0 g |
| Stearyl alcohol | 1.0 g |
| Beeswax | 1.50 g |
| Squalane | 3.0 g |
| Hydrogenated polyisobutene | 4.0 g |
| Cetearyl octanoate | 1.50 g |
| Glycerol tricaprylate/caprate | 3.0 g |
| Dimethicone | 1.0 g |
| Xanthan gum | 0.2 g |
| Carbomer | 0.15 g |
| Glycerol | 2.0 g |
| Neutralizer, preservative, perfumes, colors | qs |
| Water | qsp 100 g |

EXAMPLE 5

| Cream for sensitive skin | |
| --- | --- |
| Dry extract of Terminalia catappa leaves, methanol fraction according to Example 1 | 0.2 g |
| Methyl glucose sesquistearate | 3.0 g |
| Beeswax | 3.0 g |
| Behenyl alcohol | 3.0 g |
| Octyl octanoate | 5.0 g |
| Fluid mineral oil | 7.5 g |
| Cetostearyl octanoate | 5.0 g |
| Glycerol | 3.0 g |
| Xanthan gum | 0.50 g |
| Perfumes | 0.30 g |
| Preservative, colors | qs |
| Water | qsp 100 g |

This cream is used to firm the skin on the face and neck, while at the same time limiting the risks of the appearance of red blotches or smarting.

EXAMPLE 6

| Slimming cream | |
| --- | --- |
| Dry extract according to Example 1, methanol fraction | 0.5 g |
| Phosphate buffer | 29.5 g |
| Excipient of water-in-oil emulsion (with preservative and perfume) | qsp 100 g |

The cream thus obtained is applied once or twice a day to those parts of the body which are to be treated, such as the hips, in a one-week to three-week course of treatment.

EXAMPLE 7

| Depigmenting gel | |
| --- | --- |
| Dry extract according to Example 1, aqueous fraction | 1 g |
| Phosphate buffer | 49 g |
| Excipient of neutralized 4% Carbopol 940 ® gel, with preservatives | qsp 100 g |

This gel is applied locally to the hyperpigmented areas of the skin. It is intended particularly for the treatment of liver spots on the hands in order to reduce or eliminate them.

EXAMPLE 8
Depigmenting Gel
Aqueous solution of extract according to Example 1,

| 5% in distilled water | 4 g |
| --- | --- |
| Mulberry bark extract | 0.35 g |
| Ascorbic acid | 0.6 g |
| Carbopol 940 ® | 2 g |
| Water + preservatives | qsp 100 g |

This gel is recommended, at the start of a course of treatment, for the local treatment of freckles such as liver spots.

EXAMPLE 9
Alcoholic Hydrogel for Treating Cellulite
Aqueous solution of extract according to Example 1,

| methanol fraction | 1 g |
| --- | --- |
| Essential oil of Angelica | 0.05 g |
| Tween 80 ® | 2 g |
| Ethanol | 2 g |
| Triethylamine | 0.5 g |
| Carbopol 940 ® | 1 g |
| Water | qsp 100 g |

This preparation, when applied daily to the waist, the thighs and the hips, makes it possible to obtain a substantial reduction of the cellulite in a period of one to three weeks.

What is claimed is:

1. A method of treating skin in vivo for at least one purpose selected from the group consisting of preserving or improving biomechanical properties of the skin, treating wrinkles, improving firmness or elasticity of the skin, and dimming or vanishing freckles, comprising applying to the skin a composition comprising an effective amount of an extract of the plant *Terminalia catappa*.

2. The method according to claim 1, wherein said extract is a leaf extract.

3. The method of claim 1, wherein said composition has an inhibitory action on at least one enzyme selected from the group consisting of lipoxygenase and tyrosinase.

4. The method of claim 1, wherein said composition contains from 0.001% to 10% by weight of a dry extract of said plant.

5. The method of claim 4, wherein said composition contains from 0.02% to 1% by weight of a dry extract of said plant.

6. A method for the care of sensitive skin, and treatment of the skin manifestations of allergies and inflammation, comprising applying to the skin a composition comprising an effective amount of an extract of the plant *Terminalia catappa*.

7. The method according to claim 6, wherein said extract is a leaf extract.

8. The method of claim 6, wherein said composition has an inhibitory action on at least one enzyme selected from the group consisting of phospholipase $A_2$ and lipoxygnase.

9. The method of claim 6, wherein said composition contains from 0.001% to 10% by weight of a dry extract of said plant.

10. The method of claim 9, wherein said composition contains from 0.02% to 1% by weight of a dry extract of said plant.

* * * * *